United States Patent [19]

Evans

[11] 4,390,011
[45] Jun. 28, 1983

[54] ADJUSTABLE SURGICAL ARM REST AND INSTRUMENT PLATFORM

[76] Inventor: Daniel R. Evans, 2005 Valparaiso, Valparaiso, Ind. 46383

[21] Appl. No.: 260,891

[22] Filed: May 6, 1981

[51] Int. Cl.³ .................. A61B 19/00; A47F 5/10
[52] U.S. Cl. ................. 128/1 R; 128/303 R; 248/118; 248/118.3; 269/328; 108/6; 108/8
[58] Field of Search .............. 297/115, 116, 117, 405, 297/411, 417, 422, 173; 128/1 R, 132, 133, 134, 303 R; 269/328; 108/6, 8; 248/118, 118.1, 118.3, 405

[56] References Cited

U.S. PATENT DOCUMENTS

| | | | |
|---|---|---|---|
| 363,339 | 5/1887 | Kidder et al. | 108/8 |
| 577,202 | 2/1897 | Palmer | 108/8 |
| 2,693,635 | 11/1954 | Chapman et al. | 108/8 |
| 3,606,450 | 9/1971 | Sedgwick | 108/6 |
| 3,641,946 | 2/1972 | Charney | 108/6 |
| 4,018,217 | 4/1977 | Evans | 128/1 R |

Primary Examiner—Richard J. Apley
Assistant Examiner—Michelle N. Lester
Attorney, Agent, or Firm—Marmaduke A. Hobbs; Raymond W. Campbell

[57] ABSTRACT

An adjustable surgical arm rest and instrument platform for supporting the arms and hands of a surgeon during a micro-surgical procedure, in which a supporting platform is provided with vertical and angular adjustment mechanisms which permit rapid adjustment of the platform before, during and after the operation. Two or more platforms may be used, and each platform can be adjusted independently of the other platforms. The angular adjustment of a platform can be performed independently of the vertical adjustment of the platform. Each mechanism is provided with a two part securing feature so that the platforms will not move accidentally. An oxygen/air tube may be attached during local procedures to supply oxygen.

11 Claims, 7 Drawing Figures

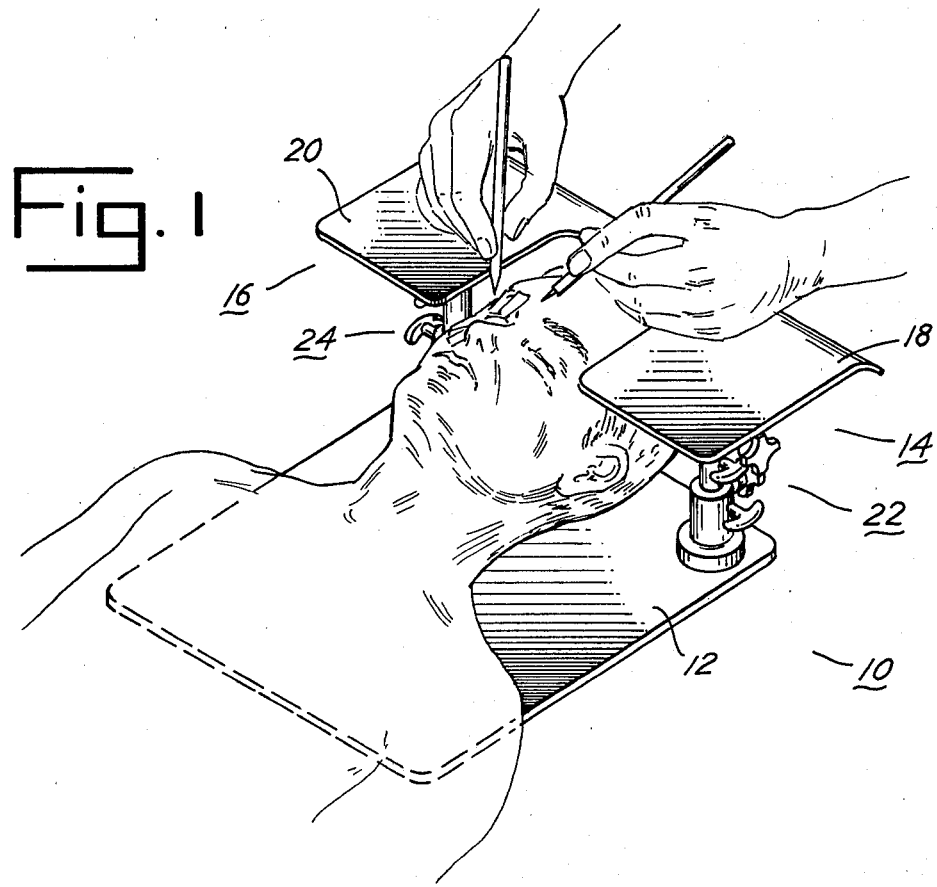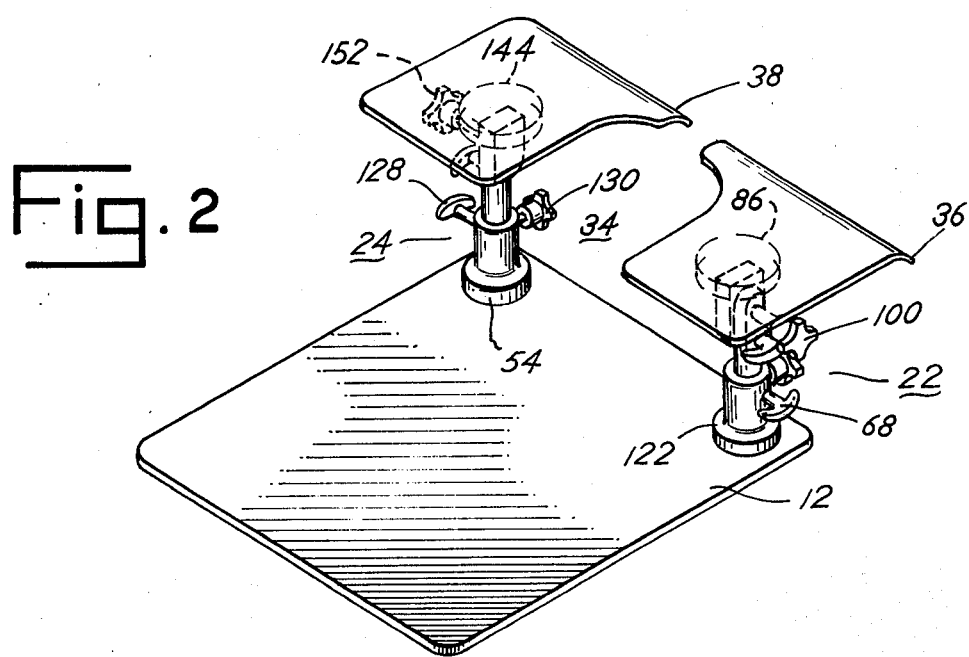

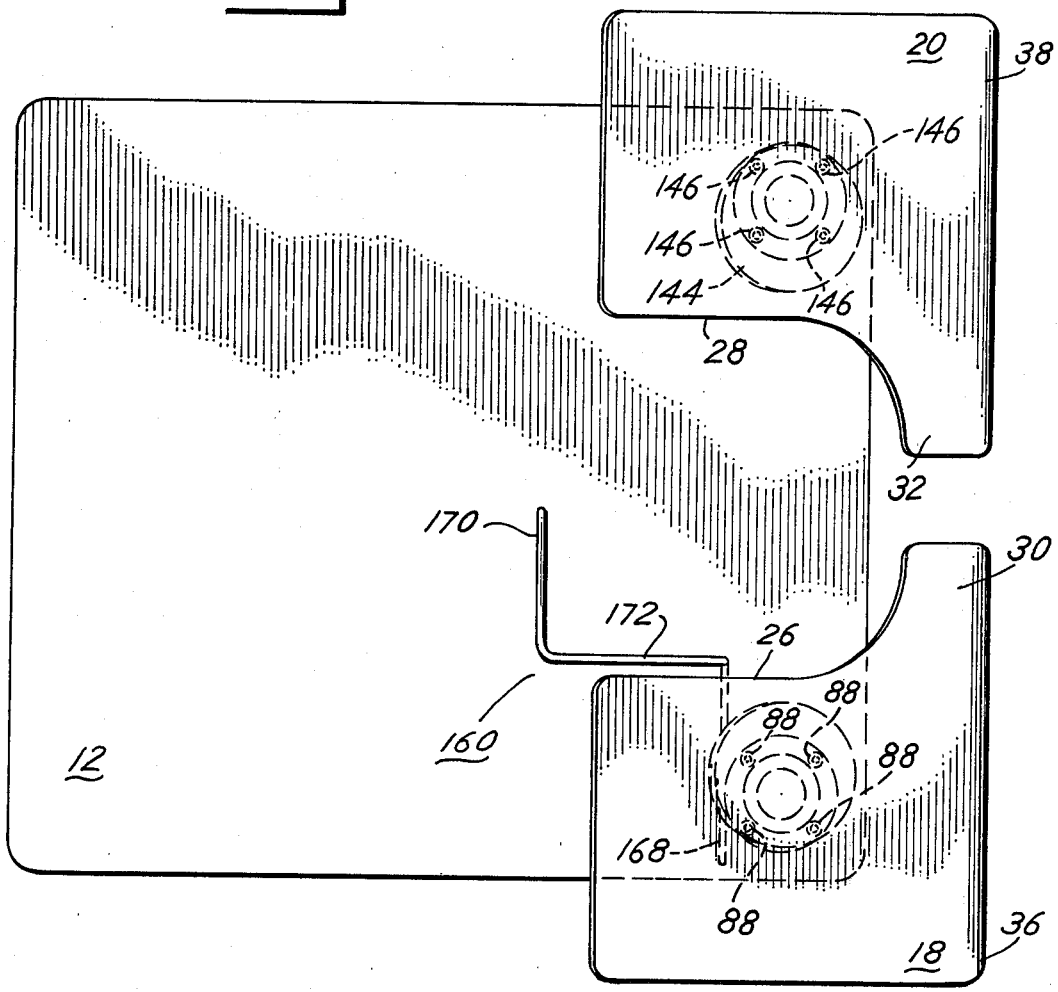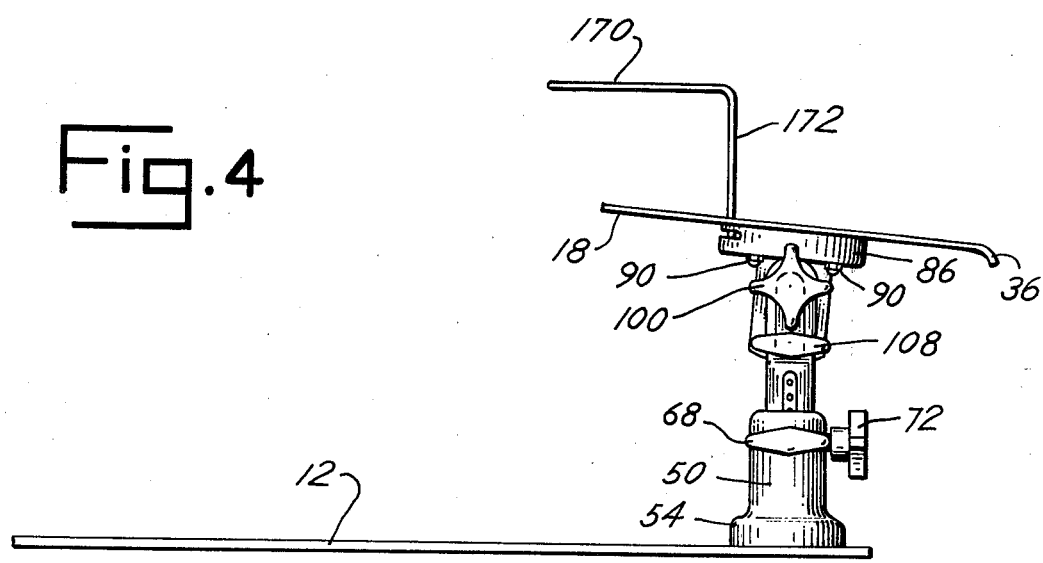

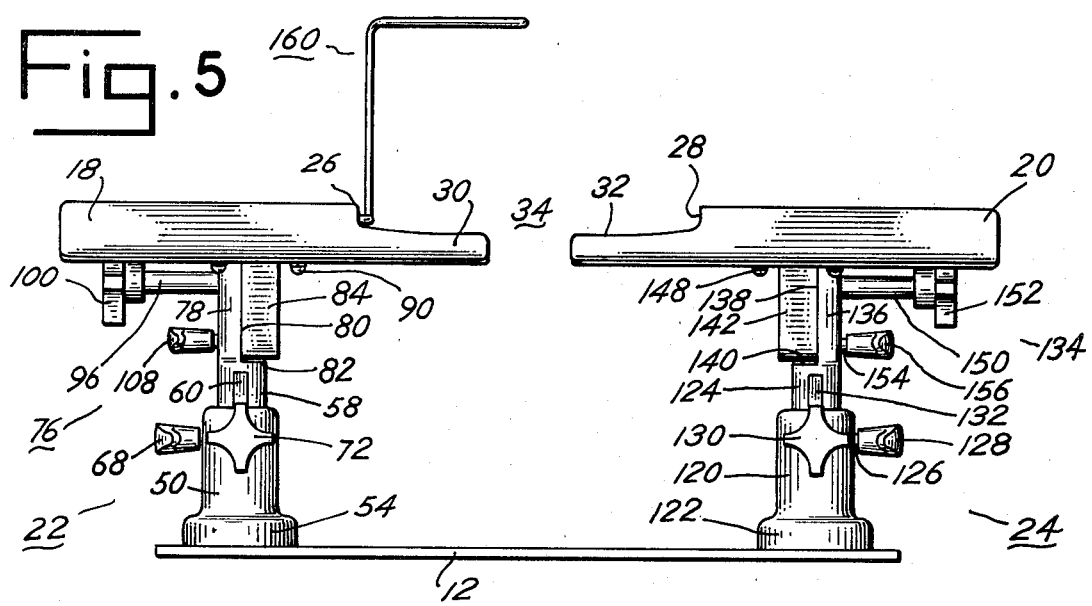
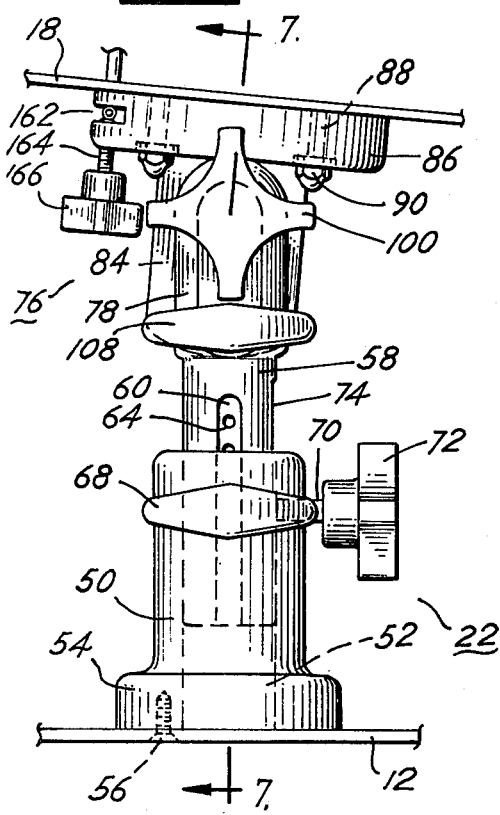
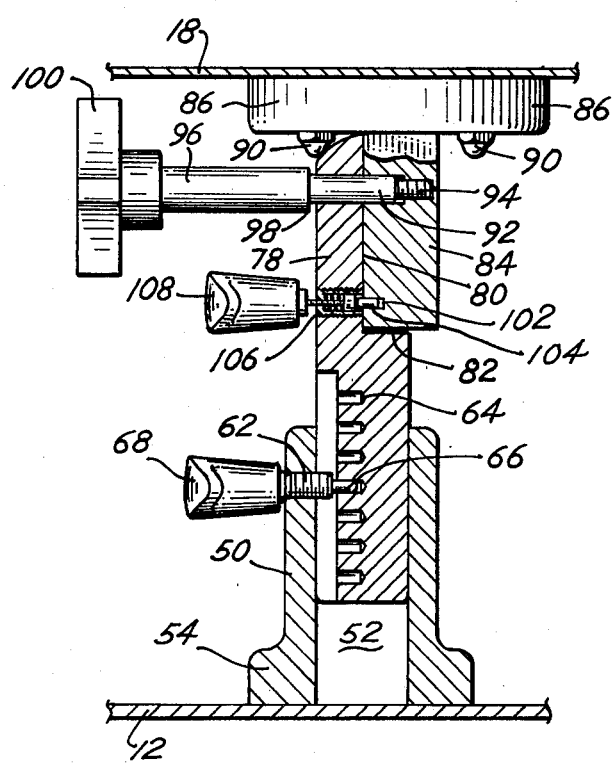

ADJUSTABLE SURGICAL ARM REST AND INSTRUMENT PLATFORM

BACKGROUND OF THE INVENTION

During the performance of micro-surgical procedures such as eye surgery, it is essential that the instruments used in and around the surgical field be held stationary, and that the surgeon's hands and arms be firmly supported when delicate and precise manipulations of instruments such as scalpel incisions are made. An inadvertent movement of an instrument or of the surgeon's arms can result in an unsuccessful operation or further injury to the patient. For a long time surgeons struggled with adapting standard surgical room equipment for use in micro-surgical procedures and obtained only limited success. Problems which were encountered included insufficient stability of the support devices and a lack of adequate adjustability to bring the surgeon's arms into comfortable positions for the operation. Also, there was no convenient place to lay instruments beside the surgical field, and no convenient way to hold the drape off the nose and mouth of the patient.

Many of the problems encountered in providing satisfactory micro-surgical support devices and instrument holding capabilities were remedied by my Arm And Hand Rest Device For Micro-Surgery, U.S. Pat. No. 4,018,217, issued Apr. 19, 1977. The device disclosed in that patent provides stable support for the surgeon's hands and arms by utilizing a board placed on the operating table beneath the patient, so that the weight of the patient holds the device firmly in place on the operating table. Legs extend upwardly from the board on each side of the area where the patient's head rests, and tables on top of the legs support the arms and/or hands of the surgeon and hold instruments so that they are readily accessible. Adjustment of the supporting surfaces is achieved by moving the patient, or the tables may be raised and lowered by turning a nut engaged on a threaded shaft in the two-part legs supporting each table.

When performing some surgical procedures the surgeon often desires to make adjustments in the height of the supporting tables during the course of the operation. Vertical adjustment can be achieved with my Arm And Hand Rest Device For Micro-Surgery; however, the adjustment procedure is often slow. When adjustment is done during an operation it is desirable that it be made quickly, and the adjustment apparatus must have a secure, fail-safe locking mechanism so that slippage of the supporting table will not occur. Further, it has been found that angular displacement of the supporting tables with respect to the board beneath the patient is often desirable. Different surgical techniques often require various arm positions for performance. Whereas one surgeon may desire to have his arms supported on a surface generally parallel with the board beneath the patient, another surgeon, or the same surgeon performing a different operation or using a different technique, may desire to have his arm supported on a surface which is angular with respect to the board beneath the patient. Hence, an angular adjustment mechanism for each of the arm rest tables is desirable, and as in the vertical adjustment mechanism, a fail-safe locking apparatus is required for the angular adjustment mechanism to prevent inadvertent movement of the tables during an operation. Further, the horizontal adjustment mechanism should enable the surgical assistants to quickly adjust the table and secure it in the adjusted position.

SUMMARY OF THE INVENTION

It is therefore one of the principal objects of the present invention to provide an adjustable surgical arm rest and instrument platform which can be used on standard operating tables for supporting the arms and hands of a surgeon or surgical assistant when micro-surgical procedures are being performed, and which may be added to or removed from the surgical table quickly, either before, during or after the performance or a micro-surgical procedure.

Another object of the present invention is to provide an adjustable surgical arm rest which includes arm and hand rest assemblies for each arm of the surgeon, and which has adjustment mechanisms for vertical and angular adjustment of the assemblies.

A further object of the present invention is to provide an adjustable surgical arm rest which can be adjusted vertically and angularly from one position to another quickly during the performance of a surgical procedure, and which includes a double locking feature in each adjustment mechanism for fail-safe adjustment of the supporting platforms.

These and other objects are accomplished in the present invention by providing a board which may be placed on an operating table beneath the head and shoulders of a patient. One or more arm and hand rest tables are disposed on the board, at the head end thereof, and include platforms which are connected to the board by pedestals having both vertical and angular adjustment mechanisms. Each adjustment mechanism includes a fixed member and a moveable member, and a locking means holds the members in adjusted positions and preferably includes a pin extending from the fixed member into any one of a number of holes in a series in the moveable member. A threaded locking screw may be used to secure the adjusted position of the platforms.

Further objects and advantages of the present invention will become apparent from the detailed description and the accompanying drawings.

BRIEF DESCRIPTION OF THE DRAWINGS

FIG. 1 is a perspective view of an adjustable surgical arm rest and instrument platform embodying the present invention, showing the proper position of a patient on the device during an eye operation;

FIG. 2 is a perspective view of the adjustable surgical arm rest and instrument platform shown in FIG. 1 with some of the concealed parts shown by broken lines;

FIG. 3 is a top plan view of the adjustable surgical arm rest and instrument platform;

FIG. 4 is a side elevational view of the adjustable surgical arm rest and instrument platform shown in the preceding figures;

FIG. 5 is an end view from the head end of the adjustable surgical arm rest and instrument platform;

FIG. 6 is an elevational view of one of the support pedestals of the arm rest and instrument platform; and FIG. 7 is a vertical cross sectional view of the support pedestal shown in FIG. 6, taken on line 7—7 of the latter figure.

DETAILED DESCRIPTION OF THE PREFERRED EMBODIMENT

Referring now more specifically to the drawings, and to FIG. 1 in particular, numeral 10 designates an adjustable surgical arm rest and instrument platform embodying the present invention, and the figure illustrates the proper use of the arm rest and the position of a patient for the performance of surgery around the face and eyes of the patient. The adjustable surgical arm rest includes a board 12 which is the same width as a standard operating table, and which is placed beneath the head and shoulders of a patient lying on an operating table. The board is held firmly in place by the weight of the patient's head and shoulders on the board. The weight of the patient's body secures the board to the operating table, illustrated in FIG. 1, the preferred manner for holding the device in position on the operating table. Adjustment of the arm rest with respect to the patient's body and head can be performed by moving board 12 before the operation, and the entire adjustable surgical arm rest is easily removed from the operating table after the operation has been completed without appreciably disturbing the patient.

Arm and hand rest assemblies 14 and 16 are mounted in the head of board 12 and include platforms 18 and 20 and pedestals 22 and 24, respectively. Platform 18 is provided with a recessed inner edge 26, and platform 20 is provided with a recessed inner edge 28 to form inwardly extending projections 30 and 32. Hence, the platforms form supporting surfaces which outline an area indicated generally by the numeral 34 in which the patient's head is positioned during an operation, and the platforms provide supporting surfaces for the hands and arms of the surgeon along the sides and the top of the patient's head. The platforms also provide convenient locations for placing surgical instruments near the surgical field. The edge of the platforms nearest the surgeon are preferably rounded, having downwardly extending portions 36 and 38.

Pedestal 22 includes a tubular or cylindrical side wall member 50 having a cylindrical bore 52 axially disposed therein. A flange 54 extends outwardly from member 50 at the bottom thereof and is attached to board 12 by screws 56 which extend through the board and are threadedly engaged with the flange. A shaft 58 is disposed in and axially moveable in bore 52. A slot 60 is disposed longitudinally in shaft 58 and a sleeve 62 extends through cylindrical member 50 and into slot 60, thereby preventing rotation of shaft 58 in bore 52. A plurality of holes 64 extend from the base of slot 60 inwardly in shaft 58, and a pin 66 extends through sleeve 62 and will engage with any one of the holes 64 which is aligned with the pin. A handle 68 is disposed on the outer end of pin 66 and a spring, not shown, in member 62 urges the pin toward shaft 58. Thus, axial movement of shaft 58 in bore 52 is prevented when pin 66 is disposed in one of the holes 64, and if the pin is in an intermediate position between holes 64, only a minimal upward or downward movement of shaft 58 will cause pin 66 to lodge in one of the holes, thereby securing the shaft with respect to its vertical position. A set screw 70 having a handle 72 on the end thereof is threadedly engaged with side wall member 50 and can be tightened inwardly in the member against a flattened surface 74 on shaft 58, thereby securing the shaft in position relative to member 50. When set screw 70 is tightened against shaft 58, the shaft will not move axially in member 50 even when pin 66 is removed from one of the holes 64, and when set screw 70 is loosened, axial movement of shaft 58 is prevented by pin 66 disposed in one of the holes 64. Thus, accidental upward or downward movement of platform 18 is not likely to occur, as a result of the double-lock feature for the axial adjustment of shaft 58 in member 50. To effect axial movement of the shaft, pin 66 must be removed from the holes in the shaft, and set screw 70 must be loosened.

Angular adjustment of platform 18 is controlled through angular adjustment mechanism 76. The upper end of shaft 58, indicated in the drawings by numeral 78, includes a recessed, flattened, vertical surface 80 and a shoulder 82 extending from surface 80 to the outer edge of the shaft. A block 84 is attached to a platform support member 86, the member 86 being attached to platform 18 by a plurality of bolts 88 connected to and extending downwardly from the platform, and nuts 90 engaged on the ends of the bolts. A shaft 92 having a threaded end 94 and an enlarged end 96 extends through upper end 78 of shaft 58, with the enlarged end 96 forming a shoulder 98 which butts against the outer surface of upper end 78. Threaded end 94 is received in a threaded opening of block 84, and turning shaft 92 to engage threaded end 94 deeper into block 84 causes shoulder 98 to butt against upper end 78 and causes block 84 to be drawn against flattened surface 80 of upper member 78. When shaft 92 is turned to withdraw threaded end 94 from block 84, the shaft operates as an axis about which block 84 can rotate, thereby changing the angle of platform 18 with respect to board 12. A handle 100 is disposed on the end of shaft 92 opposite threaded end 94 for grasping and turning the shaft.

A plurality of holes 102 are disposed near the lower end of block 84 on an arc of a circle having its center at the pivotal axis formed by shaft 92. A pin 104 is disposed through upper end 78 and is engageable with the holes 104. A spring 106 urges pin 102 toward block 84, and a handle 108 may be used to pull the pin outwardly from the holes 102. Since the holes are disposed on an arc of a circle having its center point at the axis formed by shaft 92, as the angular position of platform 18 is varied with respect to board 12, one of the holes 102 will align vertically with pin 104. Thus, even when shaft 92 is loosened so that block 84 is not held tightly against flattened surface 80, angular movement of the platform cannot occur unless pin 104 is removed from hole 102, and when the pin is removed from the hole, angular movement of the platform cannot occur unless shaft 92 is loosened and block 84 is not held tightly against surface 80.

Pedestal 24 is similar in construction to pedestal 22, being in effect the mechanical opposite thereof. Pedestal 24 includes a cylindrical member 120 and a flange 122 at the bottom thereof attached to board 12. A shaft 124 is axially moveable in cylindrical member 120, and a pin 126 having a handle 128 is received by holes, not shown, similar to holes 64, in a channel, not shown, similar to channel 60. A set screw having a handle 130 can be tightened against a flattened area 132 on shaft 124 to secure the shaft in a selected vertical position.

Pedestal 24 further includes an angular adjustment mechanism 134 including a semi-circular shaped upper end 136 of shaft 124 having a flattened vertical surface 138 and a shoulder 140. A block 142 is connected to a platform support member 144, the member 144 being connected to table 20 by bolts 146 attached to and extending downwardly from the platform and nuts 148 on the ends of the bolts. A shaft generally indicated by the numeral 150 has a threaded end, an enlarged end and a shoulder similar to the construction previously described for shaft 92. A handle 152 on the end of shaft 150 is used for rotating the shaft and tightening block 142 against flattened surfaces 138. A pin 154 urged by a spring inwardly toward block 142 is received by holes in the block, the holes not being shown in the drawings, and a handle 156 on the end of pin 154 may be used for withdrawing the pin from the holes.

During the performance of local surgical procedures it is desirable to keep the drape off the nose and mouth of the patient and to supply oxygen/air in the area beneath the drape. For this purpose, an oxygen/air tube 160 is disposed in a slot 162 in one of the platform support members. A set screw 164 having a handle 166 can be tightened against tube 160 to hold the tube in a preselected position. The tube can then be connected to a source of oxygen/air, and if the tube is of a shape similar to that shown in FIG. 3, having horizontal portions 168 and 170 with an interconnecting portion 172, the tube will assist in holding the drape off the nose and mouth of the patient while supplying oxygen/air to the patient.

In the use and operation of an adjustable surgical arm rest and instrument platform embodying the present invention, board 12 is slid between the patient and the operating table, with the patient's head and shoulders on top of the board. When eye surgery is performed using the invention, the patient's head is positioned in the area indicated generally by numeral 34, with platforms 18 and 20 on either side of the patient's head and projections 30 and 32 at the top of the patient's head. Hence, a supporting surface for the arms and hands of the surgeon is provided adjacent the patient's head. Board 12 can be repositioned between the patient and the operating table to move one or the other of arm and hand rest assemblies 14 and 16 nearer the patient's head. Vertical and angular adjustments to either of the tables are performed in a similar manner, and the description to follow will be in reference to vertical and angular adjustment of arm and hand rest assembly 14, with specific reference to the parts thereof. Adjustment of arm and hand rest assembly 16 is performed similarly to adjustment of assembly 14, by manipulating the parts of assembly 16 which correspond to the parts of assembly 14, as described hereinafter.

Vertical adjustment of platform 18 is performed by first turning handle 72 to loosen set screw 70 from flattened area 74 on shaft 58. Handle 68 is grasped and pulled outwardly to remove pin 66 from any of the holes 64 in which it is lodged. Shaft 58 can then be moved axially in bore 52 to raise or lower platform 18. Pin 66 should be held away from shaft 58 as the shaft is moved axially in bore 52 so that the pin will not lodge in any other of the holes 64 as the holes slide thereby. Shaft 58 is prevented from rotating within bore 52, in that sleeve 62 is disposed in slot 60 even when the pin is held away from the shaft and the shaft is being moved axially in bore 52. Hence, the row of holes 64 at all times remains horizontally aligned with pin 66. When platform 18 has been moved to the appropriate height, handle 68 is released, and the spring, not shown, urges pin 66 inwardly toward holes 64. When the pin lodges in one of the holes, shaft 58 cannot be moved axially in bore 52. If none of the holes 64 are vertically aligned with pin 66, the pin will be held against the bottom of slot 60 between two holes, and a slight upward or downward movement of shaft 58 will result in the pin lodging in one of the holes. After the pin lodges in one of the holes, set screw 70 is tightened against flattened area 74 of shaft 58 so that the vertical position of shaft 58 in bore 52 is secured, both by pin 66 being lodged in one of the holes 64 and by set screw 70 being tightened against the flattened area 74.

Adjustment of the angle of platform 18 relative to board 12 is achieved through operation of angular adjustment mechanism 76. Handle 100 is turned to partially withdraw threaded end 94 of shaft 92 from the threaded opening in block 84. Handle 108 is grasped and pulled outwardly to remove pin 104 from holes 102, and the platform and block assembly can be rotated about the horizontal axis formed by shaft 92 until the platform is at the desired angle relative to board 12. Handle 108 is released, and spring 106 urges pin 104 inwardly into one of the holes 102. If the holes are not properly aligned with pin 102, only a slight rotational movement of the table and block assembly about the axis formed by shaft 92 will cause one of the holes to align with the pin and the pin to lodge in the hole. Once the pin is disposed in one of the holes, angular movement of the platform about the axis formed by shaft 92 is restricted, and rotation of the shaft to turn threaded end 94 into block 84 draws the block snugly against flattened surface 80 and tightens the platform at the selected angular position.

If the oxygen/air tube is used, as in local anesthesia, tube 160 is disposed in slot 162 and is moved therein to the desired position. Set screw 164 is tightened against tube 160 to hold the tube in the selected position. The open end of horizontal portion 168 is connected to a supply source of oxygen/air, and the oxygen/air passes through the tube and is discharged through the open end of horizontal portion 170 or through a series of holes in portion 170. A drape placed over the head of the patient will be supported by the tube and held above the patient's face.

As mentioned previously, vertical and angular adjustment of arm and hand rest assembly 16 is performed in a manner similar to the procedures just described for arm and hand rest assembly 14. One of the advantages of the present adjustable surgical arm rest is that the tables are fully adjustable independently of each other, so that one platform may be higher or lower than the other and at an angle with respect to board 12 different from the angle of the other arm and hand rest assembly platform. Both the vertical and angular adjustments can be performed quickly before, during or after the surgical procedure, and accidental movement of the platforms either vertically or angularly is prevented by the double securement provided in each adjustment mechanism.

Although one embodiment of an adjustable surgical arm rest and instrument platform has been shown and described in detail herein, various changes may be made without departing from the scope of the present invention.

I claim:

1. An arm and hand rest device for performing surgery on a patient lying on an operating table, comprising a horizontally disposed board for insertion between the patient's body and the operating table, a pedestal connected to said board and having a platform at the top thereof for positioning near the head of the patient lying on the board, said pedestal having an angular adjustment mechanism for varying the angular position of the platform relative to the board, including a support member rigidly secured to said board, a bracket member attached to the platform and connected to said support member, a shaft about which the bracket member is pivotally disposed for releasably securing said support member and bracket member in adjusted positions, and a latching means including a pin extending through one of said members and received by holes in the other of said members for selecting various angular positions for said platform relative to the patient's head, and said support member and bracket member include contacting surfaces rotatable about said shaft and said shaft includes a threaded means for drawing said contacting surfaces into firm engagement with one another to assist in retaining said platform in a rigid position with respect to said pedestal.

2. An arm and hand rest device for performing surgery as defined in claim 1 in which said contacting surfaces are flat and said threaded means on said shaft is engageable with threads in said bracket member and said shaft has a shoulder engaging said support member for drawing together the flat surfaces of said support member and said bracket member.

3. An arm and hand rest device for performing surgery as defined in claim 2 in which said support member has a cylindrical base connected to the board and has an axial bore therein, and a stem axially moveable in the bore of said cylindrical base, and a locking means is provided for securing said axially moveable stem in selected positions in said cylindrical base.

4. An arm and hand rest device for performing surgery as defined in claim 3 in which said locking means for said axially moveable stem includes a pin extending inwardly in said cylindrical base and holes in said axially moveable stem for receiving the end of said pin.

5. An arm and hand rest device for performing surgery as defined in claim 4 in which a set screw is disposed in said cylindrical base and can be tightened against said axially moveable stem to prevent the axial movement thereof.

6. An arm and hand rest device for performing surgery as defined in claim 4 in which said pin is disposed in a sleeve, and said axially moveable stem includes a slot in which said sleeve is disposed for limiting rotational movement of said axially moveable stem in said cylindrical member.

7. An arm and hand rest device for performing surgery as defined in claim 1 in which said support member includes a cylindrical base connected to the board and having an axial bore therein, a stem axially moveable in said cylindrical base, and a locking means for securing said axially moveable stem in selected positions in said cylindrical member.

8. An arm and hand rest device for performing surgery as defined in claim 7 in which said threaded means on said shaft is engageable with threads in said bracket member and said shaft has a shoulder for engaging said support member for drawing together the flat surfaces of said support member and said bracket member as said threaded end is turned into said bracket member.

9. An arm and hand rest device for performing surgery as defined in claim 1 in which a second pedestal having a platform at the top thereof is connected to the board near the head of the patient, an angular adjustment mechanism connects said second pedestal and the platform at the top thereof for varying the angular position of said second mentioned platform with respect to the board, and a locking means is provided for securing the second mentioned platform in selected positions.

10. An arm and hand rest device for performing surgery as defined in claim 9 in which said second pedestal has a support member including a flat surface, a bracket member including a flat surface adjacent said first mentioned flat surface, and a shaft including a threaded end engageable with threads in said bracket member and a shoulder engaging said support member for releasably drawing said members securely together.

11. An arm and hand rest device for performing surgery as defined in claim 10 in which each of the pedestals includes a cylindrical base connected to said board and having an axial bore therein, a stem axially moveable in said cylindrical member, and a locking means for securing said axially moveable stem in selected positions in said cylindrical member.

* * * * *